United States Patent
Aizenfeld et al.

(10) Patent No.: US 6,908,428 B2
(45) Date of Patent: Jun. 21, 2005

(54) SLEEVE FOR ENDOSCOPIC TOOLS

(75) Inventors: Amram Aizenfeld, Kibutz Ramot Menashe (IL); Yakov Baror, Haifa (IL); Golan Salman, Tirat Carmel (IL); Omer Sheziffi, Haifa (IL)

(73) Assignee: Sightline Technologies Ltd., Haifa (IL)

( * ) Notice: Subject to any disclaimer, the term of this patent is extended or adjusted under 35 U.S.C. 154(b) by 70 days.

(21) Appl. No.: 10/654,701

(22) Filed: Sep. 4, 2003

(65) Prior Publication Data

US 2005/0054894 A1    Mar. 10, 2005

(51) Int. Cl.$^7$ ............................................... A61B 1/00
(52) U.S. Cl. ...................... 600/123; 600/121; 600/124
(58) Field of Search ................. 600/121–125, 600/104, 119; 604/263

(56) References Cited

U.S. PATENT DOCUMENTS

| | | |
|---|---|---|
| 3,279,460 A | 10/1966 | Sheldon |
| 3,677,262 A | 7/1972 | Zukowski |
| 3,895,637 A | 7/1975 | Choy |
| 4,066,070 A | 1/1978 | Utsugi |
| 4,077,610 A | 3/1978 | Masuda |
| 4,148,307 A | 4/1979 | Utsugi |
| 4,176,662 A | 12/1979 | Frazer |
| 4,207,872 A | 6/1980 | Meiri et al. |
| 4,321,915 A | 3/1982 | Leighton et al. |
| 4,403,985 A | 9/1983 | Boretos |
| 4,444,462 A | 4/1984 | Ono et al. |
| 4,561,427 A | 12/1985 | Takada |
| 4,646,722 A | 3/1987 | Silverstein et al. |
| 4,655,673 A | 4/1987 | Hawkes |
| 4,741,326 A | 5/1988 | Sidall et al. |
| 4,858,001 A | 8/1989 | Milbank et al. |
| 4,868,644 A | 9/1989 | Yabe et al. |
| 4,869,238 A | 9/1989 | Opie et al. |
| 4,878,485 A | 11/1989 | Adair |
| 4,884,133 A | 11/1989 | Kanno et al. |
| 4,893,613 A | 1/1990 | Hake |
| 4,967,092 A | 10/1990 | Freignier et al. |
| 5,051,824 A | 9/1991 | Nishigaki |
| 5,090,259 A | 2/1992 | Shishido et al. |
| 5,125,143 A | 6/1992 | Takahashi |
| RE34,110 E | 10/1992 | Opie et al. |
| 5,188,111 A | 2/1993 | Yates et al. |
| 5,201,908 A | 4/1993 | Jones |
| 5,203,319 A | 4/1993 | Danna et al. |
| 5,259,364 A | 11/1993 | Bob et al. |

(Continued)

FOREIGN PATENT DOCUMENTS

DE    3440177    5/1986

(Continued)

*Primary Examiner*—Beverly M. Flanagan
*Assistant Examiner*—Matthew Kasztejna
(74) *Attorney, Agent, or Firm*—Morgan & Finnegan, LLP

(57) ABSTRACT

Apparatus for sheathing an endoscopic tool includes a sheathing assembly, which includes a sleeve dispenser and a port adapter for mating with a proximal port of an endoscopic working channel so as to permit the endoscopic tool to be advanced through the sheathing assembly into the working channel. A flexible sleeve in the sheathing assembly has a distal end, which is fixed to the sleeve dispenser, and a proximal end, which is adapted to engage the endoscopic tool as the endoscopic tool is retracted from the working channel, causing the sleeve to extend out of the dispenser in a proximal direction so as to sheath the endoscopic tool.

20 Claims, 3 Drawing Sheets

U.S. PATENT DOCUMENTS

| | | |
|---|---|---|
| 5,301,061 A | 4/1994 | Nakada et al. |
| 5,365,331 A | 11/1994 | Tamburrino et al. |
| 5,372,124 A | 12/1994 | Takayama et al. |
| 5,398,670 A | 3/1995 | Ortiz et al. |
| 5,408,992 A | 4/1995 | Hamlin et al. |
| 5,483,951 A | 1/1996 | Frassica et al. |
| 5,489,256 A | 2/1996 | Adair |
| 5,538,497 A | 7/1996 | Hori |
| 5,545,169 A | 8/1996 | Yarger ......................... 606/108 |
| 5,586,968 A | 12/1996 | Grundl et al. |
| 5,626,607 A | 5/1997 | Malecki et al. |
| 5,674,182 A | 10/1997 | Suzuki et al. |
| 5,681,260 A | 10/1997 | Ueda et al. |
| 5,704,899 A | 1/1998 | Milo |
| 5,746,694 A * | 5/1998 | Wilk et al. .................. 600/123 |
| 5,817,015 A * | 10/1998 | Adair ......................... 600/121 |
| 5,819,736 A | 10/1998 | Avni et al. |
| 5,827,177 A | 10/1998 | Oneda et al. |
| 6,007,482 A | 12/1999 | Madni et al. |
| 6,007,484 A | 12/1999 | Thompson |
| 6,071,234 A | 6/2000 | Takada |
| 6,077,219 A | 6/2000 | Viebach et al. |
| 6,110,103 A | 8/2000 | Donofrio |
| 6,110,104 A | 8/2000 | Suzuki et al. |
| 6,132,211 A | 10/2000 | Peithman |
| 6,165,123 A | 12/2000 | Thompson |
| 6,174,280 B1 | 1/2001 | Oneda et al. |
| 6,241,740 B1 | 6/2001 | Davis et al. |
| 6,447,444 B1 | 9/2002 | Avni et al. |
| 6,485,409 B1 | 11/2002 | Voloshin et al. |
| 6,589,164 B1 | 7/2003 | Flaherty ..................... 600/121 |
| 6,716,159 B2 * | 4/2004 | Takase et al. ................ 600/102 |
| 2002/0017515 A1 | 2/2002 | Hidehito et al. |

FOREIGN PATENT DOCUMENTS

| | | | |
|---|---|---|---|
| DE | 296 15401 | 10/1996 | |
| EP | 0 136 539 | 8/1984 | |
| EP | 0 338557 | 4/1989 | |
| EP | 0 677 272 | 3/1995 | |
| EP | 0 745 347 | 5/1995 | |
| WO | WO 86/06944 | 5/1986 | |
| WO | WO 92/04932 | 4/1992 | .......... A61M 25/01 |
| WO | WO 94/05200 | 8/1993 | |
| WO | WO 97/04828 | 2/1997 | .......... A61M 25/01 |
| WO | WO 99/17828 | 10/1998 | |
| WO | WO 00/44275 | 1/2000 | |

* cited by examiner

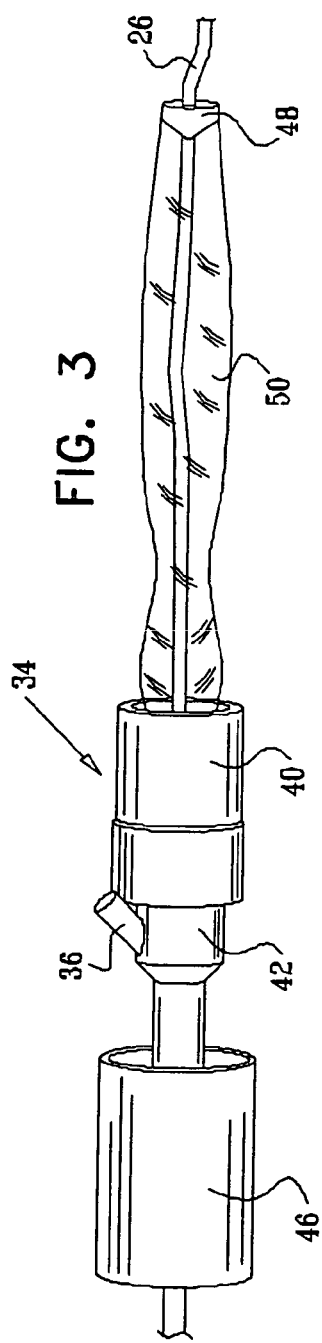
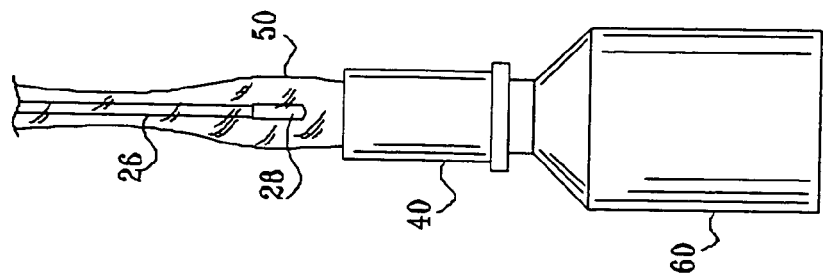

SLEEVE FOR ENDOSCOPIC TOOLS

FIELD OF THE INVENTION

The present invention relates generally to endoscopy, and specifically to the use of a disposable sleeve to cover an endoscopic tool after withdrawal of the tool from a body passage.

BACKGROUND OF THE INVENTION

The use of a disposable sleeve (also referred to as a sheath) to cover an endoscope is well known in the art. Flexible endoscopes, such as colonoscopes, are notoriously difficult to clean and disinfect thoroughly, leading to problems of cross-contamination between patients. These problems can be avoided by covering the endoscope with a single-use sleeve, which is discarded after use.

Endoscopes commonly have working channels, running from a proximal port outside the body to a distal port at the distal end of the endoscope. When the distal end of the endoscope is inserted into the body, the working channel may be used, inter alia, to pass a surgical instrument through to the distal end of the endoscope in order to perform a surgical procedure, such as a biopsy. Instruments that are used in this manner become contaminated with biological matter from inside the patient's body. As the instrument is withdrawn from the body, it can spread the contamination to the interior of the working channel and to the proximal port of the endoscope.

Methods for sheathing an endoscope while providing working channels that protect the endoscope from contamination are described, for example, in U.S. Pat. Nos. 4,646,722 and 4,741,326, whose disclosures are incorporated herein by reference. These patents attempt to prevent contamination of the endoscope, either by adding disposable working channels external to the endoscope itself (U.S. Pat. No. 4,646,722) or by adding a disposable liner inside a working channel of the endoscope (U.S. Pat. No. 4,741,326). They do not address the problem, however, of contamination that may be spread to the area around the proximal end of the endoscope as the surgical tool is retracted from the proximal port of the working channel.

SUMMARY OF THE INVENTION

Embodiments of the present invention provide methods and devices for use in sheathing an endoscopic tool as it is removed from the patient's body. Such sheathing prevents contaminants that may adhere to the tool inside the body from contacting the operator's hands, the handle of the endoscope, or other objects outside the patient's body. As a result, the likelihood of cross-contamination between patients is reduced, and the job of cleaning and disinfecting the endoscope and ancillary equipment between uses is simplified.

In embodiments of the present invention, a sheathing assembly comprising a sleeve dispenser mates with the proximal port of an endoscopic working channel, outside the patient's body. A flexible sleeve is typically fixed by its distal end to the dispenser, with the remainder of the sleeve bunched inside or otherwise held in a vicinity of the dispenser. An elongate endoscopic tool is passed through the dispenser and the working channel, until that the distal end of the tool protrudes from the distal end of the endoscope. While the shaft of the tool is advanced through the dispenser and the proximal port, the sleeve remains bunched at the dispenser. When the tool is retracted, however, the proximal end of the sleeve engages the shaft of the tool, so that as the tool is withdrawn, the sleeve unfurls from the dispenser to cover the shaft of the tool, up to and including its distal end. All contaminants on the tool thus remain within the sleeve, while the outside of the sleeve remains clean and can be handled freely without spreading contamination.

Embodiments of the present invention are particularly (although not exclusively) suited for use with sheathing systems that are used to cover the outer surface of an endoscope, such as the systems described in PCT patent application filed Aug. 7, 2003, entitled "Endoscope Sleeve Dispenser," which is incorporated herein by reference, or other systems known in the art. Such sheathing systems typically include disposable working channels or a disposable internal sleeve that fits inside the working channel of the endoscope and protects it from contamination. Endoscope sheaths of this sort cover the endoscope while the endoscope is inside the patient's body, so that the endoscope remains sterile. The sheath is removed thereafter, and the endoscope is reused.

Endoscopic tools, on the other hand, are generally allowed to become contaminated inside the body. The sheathing techniques taught by the present invention are used to cover the endoscopic tool outside the body, after it has been withdrawn from the working channel. Optionally, the tool may subsequently be advanced again distally out of the sleeve and into the working channel, and afterwards retracted back into the sleeve. When the endoscopic procedure is finished, the tool and its sleeve are disposed of together.

There is therefore provided, in accordance with an embodiment of the present invention, apparatus for sheathing an endoscopic tool, including:

a sheathing assembly, including a sleeve dispenser and a port adapter for mating with a proximal port of an endoscopic working channel so as to permit the endoscopic tool to be advanced through the sheathing assembly into the working channel; and a flexible sleeve, including a distal end, which is fixed to the sleeve dispenser, and a proximal end, which is adapted to engage the endoscopic tool as the endoscopic tool is retracted from the working channel, causing the sleeve to extend out of the dispenser in a proximal direction so as to sheath the endoscopic tool.

Typically, the endoscopic working channel with which the port adapter is adapted to mate is contained within a flexible endoscope. Alternatively, the endoscopic working channel is positioned alongside an endoscope while the endoscope is inserted into a body of a patient.

In a disclosed embodiment, the tool is adapted to extend through the working channel in order capture biological matter within a body of a patient, and after retraction of the endoscopic tool from the working channel, the sleeve dispenser is adapted to communicate with a container so as to permit the endoscopic tool to release the biological matter into the container while the endoscopic tool remains sheathed with the sleeve.

Typically, prior to retraction of the endoscopic tool from the working channel, at least a portion of the sleeve is bunched in a vicinity of the sleeve dispenser, and retracting the endoscopic tool causes the bunched portion of the sleeve to unfurl from the sleeve dispenser in the proximal direction. The sleeve dispenser and port adapter define a passage, which is aligned with the proximal port of the endoscopic working channel when the port adapter mates with the proximal port, such that the endoscopic tool passes through the bunched portion of the sleeve as the endoscopic tool is inserted through the passage into the working channel. The sheathing assembly may include a one-way plug, fixed to the proximal end of the sleeve and having an aperture therethrough, wherein the one-way plug is adapted to permit the endoscopic tool to advance through the aperture as the endoscopic tool is advanced through the sheathing assembly into the working channel, and to engage the endoscopic tool as the endoscopic tool is retracted from the working channel so as to cause the bunched portion of the sleeve to unfurl from the sleeve dispenser. Optionally, the sheathing assembly includes a channel junction, which communicates with the passage and includes a fluid port through which at least one of suction and irrigation may be applied to the working channel.

In a disclosed embodiment, the endoscopic tool includes an elongate shaft, at least a portion of which is inserted into the working channel, and a working element fixed distally to the shaft, and wherein the sleeve is adapted to cover the working element and substantially the entire portion of the shaft that was inserted into the working channel as the endoscopic tool is retracted from the working channel. Typically, the sheathing assembly and the sleeve are adapted to be detached from the proximal port and to be disposed of together with the endoscopic tool after the endoscopic tool is retracted from the working channel. Additionally or alternatively, the sheathing assembly and the sleeve are adapted to permit the endoscopic tool to be advanced repeatedly through the sheathing assembly into the working channel after the endoscopic tool is retracted from the working channel, while the sleeve covers the portion of the shaft that was previously inserted into the working channel and continues to extend out of the dispenser in the proximal direction.

There is also provided, in accordance with an embodiment of the present invention, a method for sheathing an endoscopic tool, including:

connecting a distal end of a flexible sleeve to a proximal port of an endoscopic working channel so as to permit the endoscopic tool to be advanced through the sleeve into the working channel; and coupling a proximal end of the flexible sleeve to engage the endoscopic tool as the endoscopic tool is retracted from the working channel, so as to cause the sleeve to extend away from the proximal port in a proximal direction in order to sheath the endoscopic tool. The present invention will be more fully understood from the following detailed description of the embodiments thereof, taken together with the drawings in which:

BRIEF DESCRIPTION OF THE DRAWINGS

FIG. 3 is a schematic, pictorial illustration showing retraction of an endoscopic tool through a sheathing assembly, in accordance with an embodiment of the present invention; and FIG. 4 is a schematic, pictorial illustration showing transfer of a tissue sample from an endoscopic tool to a sample container, in accordance with an embodiment of the present invention.

DETAILED DESCRIPTION OF EMBODIMENTS

Figure 1:
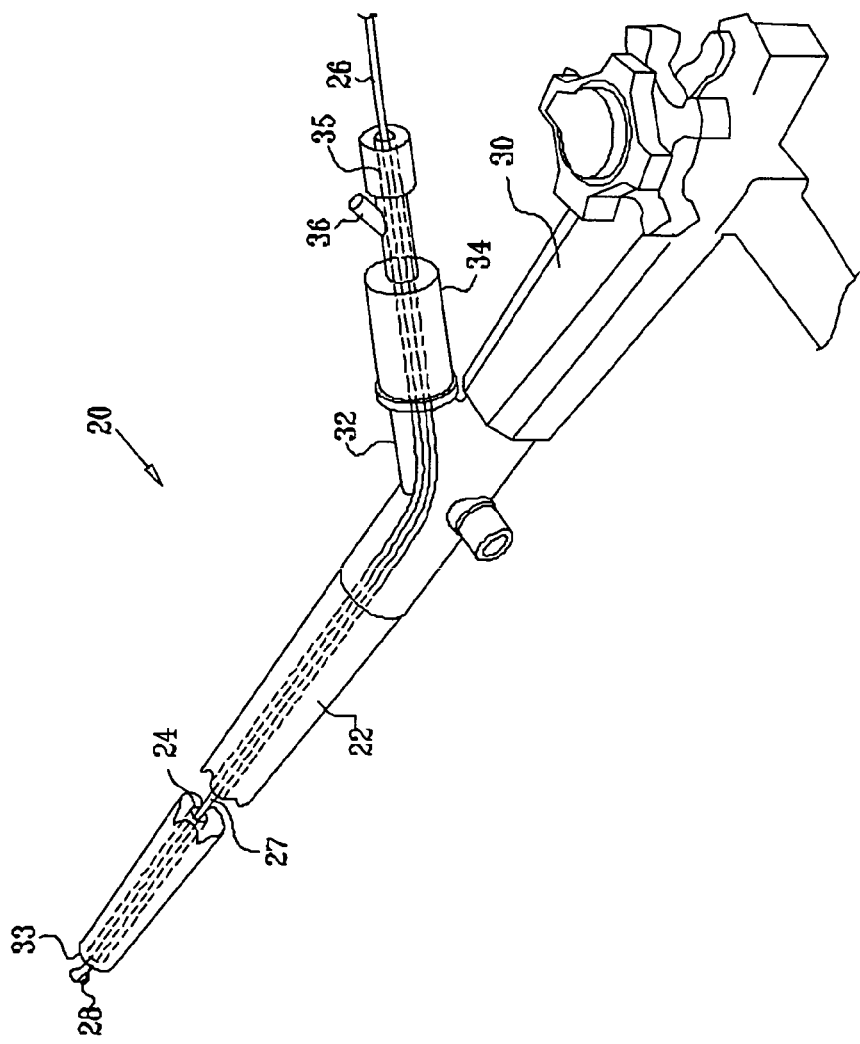
FIG. 1 is a schematic, pictorial illustration of a system for performing an endoscopic procedure, in accordance with an embodiment of the present invention.

FIG. 1 is a schematic, pictorial illustration of a system 20 for performing an endoscopic procedure, in accordance with an embodiment of the present invention. System 20 comprises an endoscope 22, having a working channel 24 passing therethrough. Channel 24 passes through endoscope 22 from a proximal port 32, typically in or near a handle 30 of the endoscope, to a distal port 33 at the distal end of the endoscope. An endoscopic tool 26 is inserted through channel 24 in order to access an area adjacent to the distal end of the endoscope, within the patient's body. Typically, tool 26 comprises an elongate shaft 27, with a working element 28 at its distal end, as is known in the art. In the example shown in FIG. 1, working element 28 comprises biopsy forceps, which are operable to take a tissue sample within the patient's body, adjacent to distal port 33. Alternatively or additionally, channel 24 may be used to apply suction through distal port 33 or to apply fluid or gas to the area outside the distal port, as is likewise known in the art.

Endoscope 22 may be covered by a disposable sheath, and channel 24 may likewise be internally sheathed, in order to protect the endoscope from contamination, as described in the above-mentioned U.S. Pat. No. 4,741,326 or PCT patent application entitled "Endoscope Sleeve Dispenser." Such sheathing is omitted from FIG. 1, however, for the sake of simplicity. Alternatively or additionally, although channel 24 is shown in the figure as passing inside the endoscope, the endoscopic working channel may comprise a separate tube, typically disposable, which is fixed alongside the endoscope, as described, for example, in the above-mentioned U.S. Pat. No. 4,646,722. The present invention is suited for use with either of these types of working channels.

Since at least working element 28 of tool 26 comes into contact with tissue and other biological matter inside the patient's body, the tool and the interior of the working channel (or the internal sheath lining the working channel) necessarily become contaminated during use. In order to prevent the spread of contamination from tool 26 to handle 30, to the operator's hands and to other areas outside the body, a sheathing assembly 34 is fitted onto port 32. The use of sheathing assembly 34 is described in detail with reference to the figures that follow. Typically, assembly 34 mates with port 32 so that a passage 35 through the assembly is aligned with working channel 24. Tool 26 is then inserted through passage 35 into working channel 24 and can be used in the usual manner. Assembly 34 may also comprise a fluid port 36, for use in applying suction, gas pressure and/or irrigation through channel 24, typically when tool 26 is not inserted in the working channel. Additionally or alternatively, assembly 34 may comprise additional ports (not shown), for mating with additional channels within or alongside endoscope 22.

Figure 2:
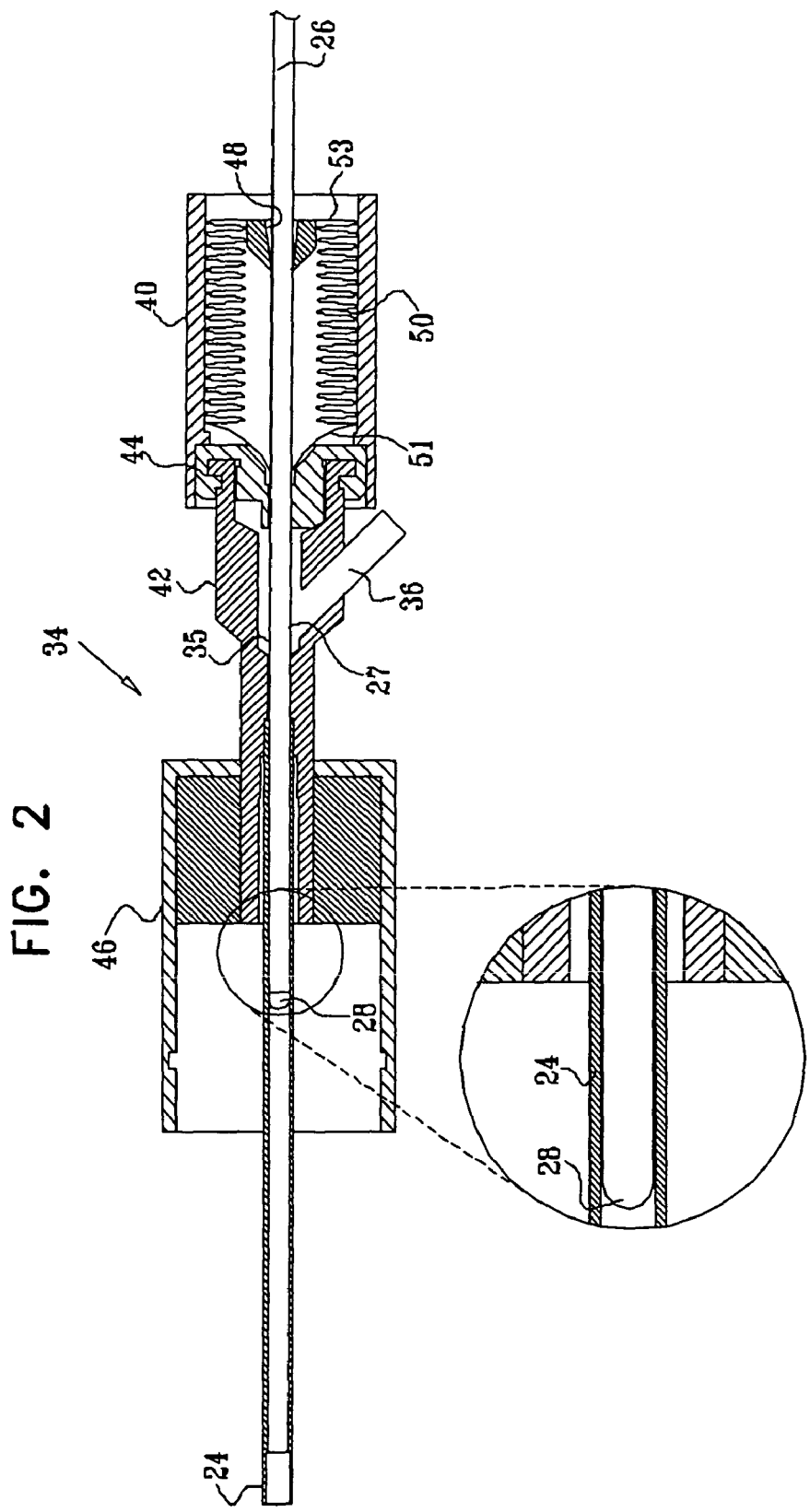
FIG. 2 is a schematic, sectional view of an assembly for sheathing an endoscopic tool, in accordance with an embodiment of the present invention.

FIG. 2 is a schematic, sectional view of sheathing assembly 34, in accordance with an embodiment of the present invention. Assembly 34 is shown as comprising several separable parts, whose functions are described hereinbelow. Alternatively, assembly 34 may comprise a single, integral unit or may be divided into different functional sections, as will be apparent to those skilled in the art. In the present embodiment, a sleeve dispenser 40 holds a flexible sleeve 50, which is initially bunched inside dispenser 40. Typically, sleeve 50 comprises a flexible, biocompatible plastic, such as polyamide, having a thickness of about 20 µm. Dispenser 40 is joined to a channel junction 42, which also comprises fluid port 36, by an elastic coupler 44. Junction 42 is fixed to a port adapter 46, which mates with proximal port 32 of endoscope 22, as shown in FIG. 1. Typically, dispenser 40, junction 42 and adapter 46 comprise rigid plastic material, such as PVC, while coupler 44 comprises a softer, elastic material, such as silicone.

Sleeve 50 is anchored at a distal end 51 thereof (i.e., at its left side in the view shown in FIG. 2) to dispenser 40, while a proximal end 53 (right side) is fixed to a plug 48. Plug 48 typically comprises an elastic material, such as silicone, and contains an aperture that fits snugly around shaft 27 of tool 26. The plug is designed so that shaft 27 of tool 26 may be advanced through the plug in the distal direction—into the patient's body—with little resistance. When the tool is retracted in the proximal direction, however, plug 48 catches on the shaft, causing the plug, and sleeve 50 along with it, to be pulled out of assembly 40 in the proximal direction, as shown in the figures that follow. For this purpose, the aperture in plug 48 may be suitably tapered, as shown in the figure. Alternatively, other types of one-way plugs may be used, as will be apparent to those skilled in the art.

As shown in the inset in FIG. 2, working channel 24 may protrude out of proximal port 32 into sheathing assembly 34. Alternatively, the sheathing assembly may accommodate the proximal end of an internal sleeve (not shown), which is used to line working channel 24, as described above. The proximal end of the working channel or sleeve mates with junction 42, so that tool 26 is contained entirely within working channel 24 and sheathing assembly 34. Sheathing assembly 34 may similarly be adapted to mate with a disposable working channel, external to the endoscope.

FIG. 3 is a schematic, pictorial illustration showing retraction of tool 26 through sheathing assembly 34, in accordance with an embodiment of the present invention. Plug 48 grasps shaft 27 as the tool is retracted in the proximal direction (toward the right in the figure), causing sleeve 50 to unfurl gradually and feed out of dispenser 40 along with the shaft of the tool. Typically, while the tool is retracted, the plug remains fixed to shaft 27 at the most proximal point on the shaft that reached the plug as the tool was advanced into assembly 34. Therefore, as tool 26 is retracted, the entire length of shaft 27 that previously entered working channel 24 is sheathed by sleeve 50, up to and including working element 28. If desired, after the tool has been retracted (in whole or in part), it may repeatedly be advanced into the working channel without removing the tool from sleeve 50, and then retracted again thereafter. In this situation, the sleeve continues to cover any portion of shaft 27 that was previously inserted into the working channel (and is therefore contaminated), but now extends out of the dispenser in the proximal direction. Once tool 26 has been completely retracted from the endoscope and, simultaneously, sheathed by sleeve 50, assembly 34 may be detached from port 32 and disposed of, along with the tool.

FIG. 4 is a schematic, pictorial illustration showing transfer of a tissue sample from working element 28 of tool 26 to a sample container 60, in accordance with an embodiment of the present invention. In this embodiment, tool 26 has been retracted completely from endoscope 22, and sheathing assembly 34 has been detached from port 32. Dispenser 40 is then disconnected from junction 42 and is coupled to the neck of container 60, as shown in the figure. At this point, assuming working element 28 to comprise biopsy forceps holding a biopsy sample captured inside the patient's body, for example, the operator of tool 26 may advance element 28 into the neck of container 60, and may then open the forceps, releasing the biopsy sample into the container. Thus, working element 28 and the sample that it captures are never exposed to the environment outside sleeve 50 and container 60.

Sheathing assembly 34 is particularly suited for use with flexible endoscopes that are inserted into the gastrointestinal tract, such as colonoscopes and gastroscopes, which have relatively large working channels. Alternatively, the principles of the present invention may be applied to sheath tools that are inserted through lumens in medical probes of other types, such as endoscopes (both rigid and flexible) and catheters used in other body passages and in other therapeutic and diagnostic procedures.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for sheathing an endoscopic tool, comprising:
   a sheathing assembly, comprising a sleeve dispenser and a port adapter for mating with a proximal port of an endoscopic working channel so as to permit the endoscopic tool to be advanced through the sheathing assembly into the working channel; and
   a flexible sleeve, comprising a distal end, which is fixed to the sleeve dispenser, and a proximal end, which is adapted to engage the endoscopic tool as the endoscopic tool is retracted from the working channel, causing the sleeve to extend out of the dispenser in a proximal direction so as to sheath the endoscopic tool.

2. The apparatus according to claim 1, wherein the endoscopic working channel with which the port adapter is adapted to mate is contained within a flexible endoscope.

3. The apparatus according to claim 1, wherein the endoscopic working channel with which the port adapter is adapted to mate is positioned alongside an endoscope while the endoscope is inserted into a body of a patient.

4. The apparatus according to claim 1, wherein the tool is adapted to extend through the working channel in order capture biological matter within a body of a patient, and wherein after retraction of the endoscopic tool from the working channel, the sleeve dispenser is adapted to communicate with a container so as to permit the endoscopic tool to release the biological matter into the container while the endoscopic tool remains sheathed with the sleeve.

5. The apparatus according to claim 1, wherein prior to retraction of the endoscopic tool from the working channel, at least a portion of the sleeve is bunched in a vicinity of the sleeve dispenser, and wherein retracting the endoscopic tool causes the bunched portion of the sleeve to unfurl from the sleeve dispenser in the proximal direction.

6. The apparatus according to claim 5, wherein the sleeve dispenser and port adapter define a passage, which is aligned with the proximal port of the endoscopic working channel when the port adapter mates with the proximal port, such that the endoscopic tool passes through the bunched portion of the sleeve as the endoscopic tool is inserted through the passage into the working channel.

7. The apparatus according to claim 6, wherein the sheathing assembly comprises a one-way plug, fixed to the proximal end of the sleeve and having an aperture therethrough, wherein the one-way plug is adapted to permit the endoscopic tool to advance through the aperture as the endoscopic tool is advanced through the sheathing assembly into the working channel, and to engage the endoscopic tool as the endoscopic tool is retracted from the working channel so as to cause the bunched portion of the sleeve to unfurl from the sleeve dispenser.

8. The apparatus according to claim 6, wherein the sheathing assembly comprises a channel junction, which communicates with the passage and comprises a fluid port through which at least one of suction and irrigation may be applied to the working channel.

9. The apparatus according to claim 1, wherein the endoscopic tool includes an elongate shaft, at least a portion of which is inserted into the working channel, and a working element fixed distally to the shaft, and wherein the sleeve is adapted to cover the working element and substantially the entire portion of the shaft that was inserted into the working channel as the endoscopic tool is retracted from the working channel.

10. The apparatus according to claim 9, wherein the sheathing assembly and the sleeve are adapted to be detached from the proximal port and to be disposed of together with the endoscopic tool after the endoscopic tool is retracted from the working channel.

11. The apparatus according to claim 9, wherein the sheathing assembly and the sleeve are adapted to permit the endoscopic tool to be advanced repeatedly through the sheathing assembly into the working channel after the endoscopic tool is retracted from the working channel, while the sleeve covers the portion of the shaft that was previously inserted into the working channel and continues to extend out of the dispenser in the proximal direction.

12. A method for sheathing an endoscopic tool, comprising:
connecting a distal end of a flexible sleeve to a proximal port of an endoscopic working channel so as to permit the endoscopic tool to be advanced through the sleeve into the working channel; and
coupling a proximal end of the flexible sleeve to engage the endoscopic tool as the endoscopic tool is retracted from the working channel, so as to cause the sleeve to extend away from the proximal port in a proximal direction in order to sheath the endoscopic tool.

13. The method according to claim 12, wherein the endoscopic working channel to which the sleeve is connected is contained within a flexible endoscope.

14. The method according to claim 12, wherein the endoscopic working channel to which the sleeve is connected is positioned alongside an endoscope while the endoscope is inserted into a body of a patient.

15. The method according to claim 12, and comprising:
inserting the endoscopic tool through the working channel in order capture biological matter within a body of a patient;
retracting the endoscopic tool from the working channel after capturing the biological matter; and
after retraction of the endoscopic tool from the working channel, coupling the sleeve to communicate with a container so as to permit the endoscopic tool to release the biological matter into the container while the endoscopic tool remains sheathed with the sleeve.

16. The method according to claim 12, wherein connecting the distal end of the flexible sleeve comprises bunching at least a portion of the sleeve in a vicinity of the proximal port so that the endoscopic tool passes through the bunched portion of the sleeve as the endoscopic tool is inserted into the working channel, and
wherein coupling the proximal end of the flexible sleeve comprises causing the bunched portion of the sleeve to unfurl in the proximal direction responsively to retraction of the endoscopic tool from the working channel.

17. The method according to claim 16, wherein coupling the proximal end of the flexible sleeve comprises fixing a one-way plug to the proximal end of the sleeve, wherein the one-way plug has an aperture therethrough and is adapted to permit the endoscopic tool to advance through the aperture as the endoscopic tool is advanced through the sheathing assembly into the working channel, and to engage the endoscopic tool as the endoscopic tool is retracted from the working channel so as to cause the bunched portion of the sleeve to unfurl from the sleeve dispenser.

18. The method according to claim 12, wherein the endoscopic tool includes an elongate shaft, at least a portion of which is inserted into the working channel, and a working element fixed distally to the shaft, and wherein coupling the proximal end of the flexible sleeve to engage the endoscopic tool comprises coupling the flexible sleeve so that as the endoscopic tool is retracted from the working channel, the sleeve covers the working element and substantially the entire portion of the shaft that was inserted into the working channel.

19. The method according to claim 18, and comprising detaching the sleeve from the proximal port after retraction of the endoscopic tool from the working channel, and disposing of the sleeve together with the endoscopic tool while substantially the entire portion of the shaft that was inserted into the working channel is covered by the sleeve.

20. The method according to claim 12, comprises arranging the sleeve to permit the endoscopic tool to be repeatedly advanced into the working channel after the endoscopic tool is retracted from the working channel, while the sleeve covers the portion of the shaft that was previously inserted into the working channel and continues to extend out of the dispenser in the proximal direction.

* * * * *

UNITED STATES PATENT AND TRADEMARK OFFICE
CERTIFICATE OF CORRECTION

PATENT NO. : 6,908,428 B2  Page 1 of 1
DATED : June 21, 2005
INVENTOR(S) : Aizenfeld et al.

It is certified that error appears in the above-identified patent and that said Letters Patent is hereby corrected as shown below:

Column 6,
Line 44, after "order" insert -- to --.

Column 7,
Line 53, after "order" insert -- to --.

Signed and Sealed this

Second Day of May, 2006

JON W. DUDAS
*Director of the United States Patent and Trademark Office*